(12) United States Patent
Guillon et al.

(10) Patent No.: US 9,290,704 B2
(45) Date of Patent: Mar. 22, 2016

(54) FLEXIBLE PROCESS FOR TRANSFORMATION OF ETHANOL INTO MIDDLE DISTILLATES IMPLEMENTING A HOMOGENEOUS CATALYTIC SYSTEM AND A HETEROGENEOUS CATALYTIC SYSTEM

(75) Inventors: Emmanuelle Guillon, Vourles (FR); Nicolas Cadran, Oullins (FR); Natacha Touchais, Vienne (FR); Laurent Bournay, Chaussan (FR); Lionel Magna, Lyons (FR); Helene Olivier-Bourbigou, Saint Genis-Laval (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 809 days.

(21) Appl. No.: 13/102,384

(22) Filed: May 6, 2011

(65) Prior Publication Data

US 2011/0313221 A1 Dec. 22, 2011

(30) Foreign Application Priority Data

May 6, 2010 (FR) ...................................... 10 01954

(51) Int. Cl.
*C10G 50/00* (2006.01)
*C10G 1/00* (2006.01)
*C10G 3/00* (2006.01)

(52) U.S. Cl.
CPC *C10G 50/00* (2013.01); *C10G 3/49* (2013.01); *C10G 3/62* (2013.01);
(Continued)

(58) Field of Classification Search
USPC ....................................................... 585/324
See application file for complete search history.

(56) References Cited

U.S. PATENT DOCUMENTS 4,283,305 A 8/1981 Chauvin et al.
4,362,650 A * 12/1982 Chauvin et al. ............... 502/117
(Continued)

FOREIGN PATENT DOCUMENTS

EP 0 012 685 A1 6/1980
EP 2 123 736 A1 11/2009
(Continued)

OTHER PUBLICATIONS

Sinnott, R. K., Coulson & Richardson's Chemical Engineering, Chemical Engineering Design, vol. 6 Fourth Edition, 2005 Elsevier, p. 50.*

(Continued)

*Primary Examiner* — In Suk Bullock
*Assistant Examiner* — Philip Louie
(74) *Attorney, Agent, or Firm* — Millen, White, Zelano, Branigan, P.C.

(57) ABSTRACT

The invention describes a process for the production of middle distillate hydrocarbon bases from an ethanol feedstock that is produced from a renewable source that is obtained from biomass, comprising a stage for purification of said feedstock, a stage for dehydration of said purified feedstock into an effluent that is for the most part ethylene and comprises water, at least one stage for separating water, a first stage for oligomerization of the effluent that is for the most part ethylene into at least one olefinic effluent that comprises at least 80% by weight of olefins that have four or more carbon atoms, in the presence of a homogeneous catalyst that comprises at least one bivalent nickel compound, whereby a second oligomerization stage produces middle distillate hydrocarbon bases in the presence of an amorphous or zeolitic catalyst that has at least pore openings that contain 10 or 12 oxygen atoms, producing middle distillate hydrocarbon bases, and a fractionation stage.

32 Claims, 2 Drawing Sheets

(52) U.S. Cl.
CPC . *C10G 2300/1014* (2013.01); *C10G 2300/301* (2013.01); *C10G 2400/04* (2013.01); *C10G 2400/08* (2013.01); *Y02P 30/20* (2015.11)

(56) References Cited

U.S. PATENT DOCUMENTS

| | | | |
|---|---|---|---|
| 4,387,262 A * | 6/1983 | Chauvin et al. | 585/523 |
| 4,538,018 A | 8/1985 | Carter | |
| 4,547,601 A * | 10/1985 | Holland et al. | 585/310 |
| 4,698,452 A * | 10/1987 | Le Van Mao et al. | 585/640 |
| 6,444,866 B1 * | 9/2002 | Commereuc et al. | 585/517 |
| 2005/0192471 A1 | 9/2005 | Commereuc et al. | |
| 2006/0063955 A1 * | 3/2006 | Lacombe et al. | 585/535 |
| 2010/0312031 A1 * | 12/2010 | Heidemann | C07C 2/08 585/326 |

FOREIGN PATENT DOCUMENTS

| | | |
|---|---|---|
| GB | 2 326 885 A | 1/1999 |
| WO | WO 2009/079213 A2 | 6/2009 |
| WO | WO 2009079213 A2 * | 6/2009 |

OTHER PUBLICATIONS

M A Bawase, S D Reve, S V Shete and M R Saraf, Carbon Number Distribution by Gas Chromatographyfor Identification of Outlying Diesel Sample, AdMet 2012 Paper No. CM 003, p. 1-7.*
Search Report of FR 1001954 (Dec. 6, 2010).

* cited by examiner

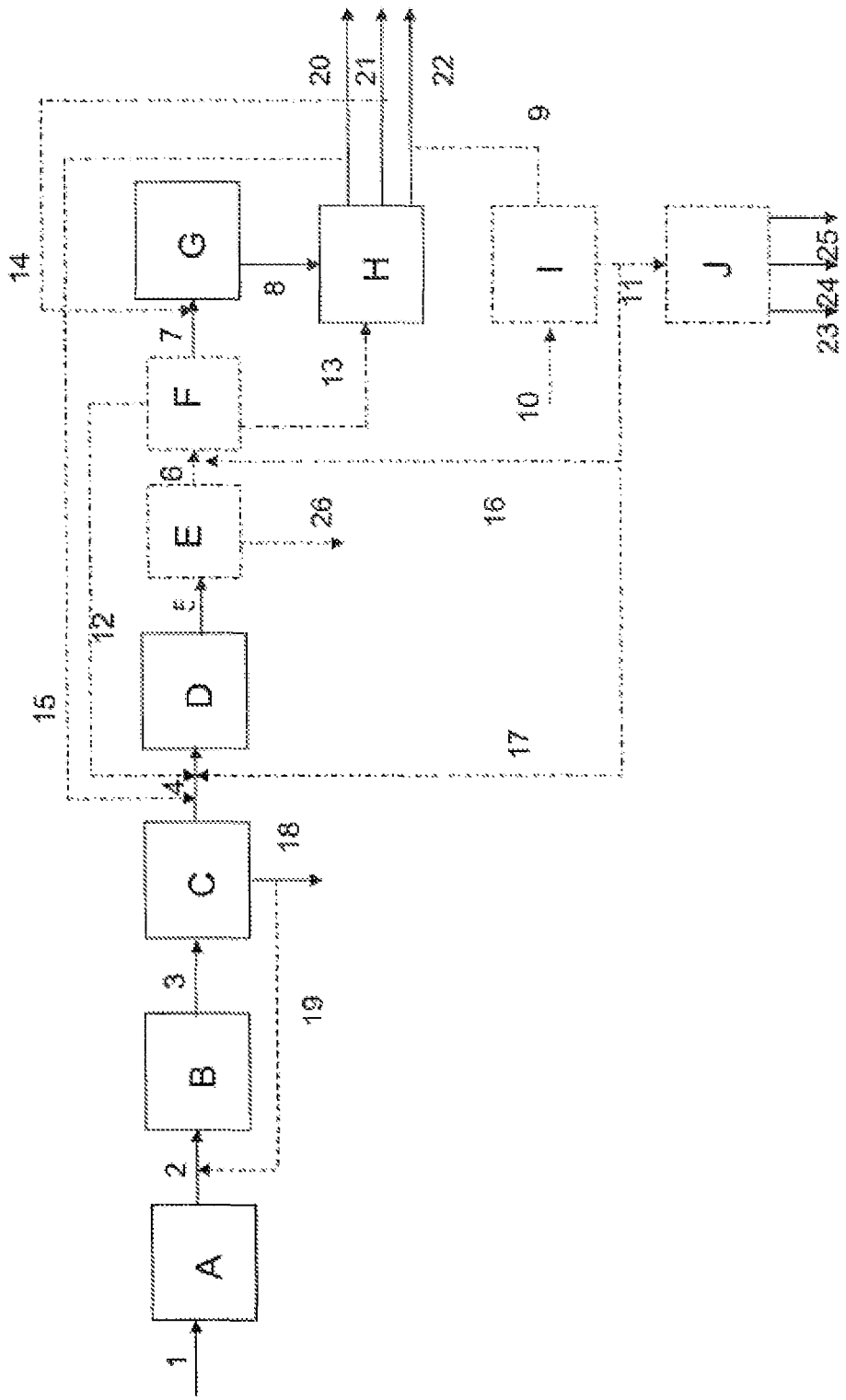

FLEXIBLE PROCESS FOR TRANSFORMATION OF ETHANOL INTO MIDDLE DISTILLATES IMPLEMENTING A HOMOGENEOUS CATALYTIC SYSTEM AND A HETEROGENEOUS CATALYTIC SYSTEM

FIELD OF THE INVENTION

This invention relates to the transformation of ethanol, and more particularly bioethanol, into a fuel base.

It relates more particularly to a flexible catalytic process for transformation of ethanol into middle distillates.

PRIOR ART

The demand for use of biomass as a partial replacement of petroleum resources for the synthesis of fuels continues to grow. Thus, the use of bioethanol for the synthesis of bases for fuels is gaining more and more active interest.

Bioethanol is the ethanol of agricultural origin; i.e., it is produced from a renewable source that is obtained from biomass, such as, for example, living plant materials.

The major portion of ethanol is produced by fermentation of sugars contained in the raw materials of plant origin. Starting from sugar plants, the first stage of the transformation consists in obtaining a sugary juice by extraction with hot water for beet scraps or by grinding and pressing for sugar cane. After optional concentration, these juices, or syrup, are introduced into fermenters where the biological transformation of sugars into ethanol takes place with the co-production of $CO_2$ under the action of microorganisms (yeasts). The wines that are obtained contain approximately 10% alcohol in water. One distillation stage makes it possible to produce the azeotropic composition of the ethanol/water binary (8% water). So as to achieve complete dehydration, being run over a molecular sieve is necessary. In grain plants (corn, wheat), the sugars that can ferment into ethanol are present in the form of a polymer called starch; for releasing them, a preliminary stage of hydrolysis catalyzed by enzymes is necessary.

New technologies are being developed so as to allow the transformation of the lignocellulosic biomass (wood, grass, straw and other agricultural waste, etc.) into bioethanol.

Ethanol can be used as a biofuel in gasoline engines. This product has significant advantages: high octane number, a miscibility of any proportion in gasoline and a close density. It is an energy vector that is obtained from agriculture and that belongs to the family of renewable energies. There are several types of fuels that contain ethanol; most of them are mixtures of gasoline and ethanol in different proportions. They are designated by the letter E followed by the percentage of ethanol in the mixture: for example, E85 represents a fuel that contains 85% ethanol and 15% gasoline. In this nomenclature, E100 designates pure ethanol. Thus, there are E5, E7, E10, E15, E20, E85, E95, and E100 based on the country in which they are located and the use that it is desired to make of them.

In France, the marketing of E85, legally named superethanol, to private individuals has been official since Jan. 1, 2007.

In Europe, the oil-producing countries continue to transform ethanol into ETBE (ethyl tert-butyl ether), which can be incorporated in gasoline to a level of 15%. The ETBE offers the advantage of being better suited to engines. Actually, the direct incorporation of ethanol in gasoline poses certain technical problems: the gasoline/ethanol mixture has an elevated vapor pressure and poorly tolerates the presence of traces of water. These problems can be overcome by a reformulation of gasoline bases and by the elimination of traces of water in the tanks. Nevertheless, ETBE is not as good for the environment. The European vehicle fleet is characterized by a large proportion of diesel vehicles; the result is that the gas oil is consumed in a very large proportion relative to gasoline. The biofuels that can be incorporated in the gas oil pool are therefore particularly appreciated in Europe.

The use of ethanol is essentially designed for the production of gasoline and not for the production of gas oils and kerosenes. Another very promising method is the use of ethanol as a biofuel in diesel engines. The E-diesel biofuel is a mixture that consists of diesel between 85% and 95%, anhydrous ethanol (without water), and a package of additives that is specially produced for the stability of the mixture and for eliminating some of the drawbacks of the bioethanol, such as, for example, its low cetane number, and its low lubricating power.

Mixing the conventional diesel with ethanol and the additive improves the operation of the combustion and slightly increases the volatility of the fuel. The primary result is the reduction of regulated gas pollutant emissions such as particulates (PM10) and smoke. This reduction is due to the oxygen content of the biofuel that limits the formation of particulates during the combustion of the fuel. Actually, these oxidized molecules make possible a significant improvement of the quality of the combustion by the presence of oxidizer at the very location where the oxidation reaction is done. The mixture of bioethanol with diesel also has as its consequence and primary drawback the reduction of the flash point.

The transformation of ethanol into hydrocarbons is therefore an advantageous way to upgrade the renewable resources to fuels.

There is a great deal of literature on the transformation of methanol-type alcohols into olefins or aromatic compounds for producing a gasoline fraction on acid catalysts, often zeolitic catalysts.

The production of ethylene from ethanol is a known process that was developed on the industrial scale on several units. Thus, units for dehydrating ethanol into ethylene were constructed in Brazil during the 1970s in the wake of the oil crisis. Ethanol is converted catalytically into ethylene starting from 300° C. The catalysts that are used can be of different natures: activated alumina, silica alumina, . . . .

Scientific Design developed its own technology for dehydrating ethanol into ethylene and in the wake of the development of a new catalyst, introduced on an industrial unit, published an article ("Ethylene from Ethanol," N. K. Kochar, R. Merims, and A. S. Padia, CEP, June 1981). The U.S. Pat. Nos. 4,232,179, 4,396,789, 4,234,752, 4,396,789, and 4,698,452 can also be cited.

One objective of this invention is to provide a process for the production of middle distillate hydrocarbon bases (gas oil and/or kerosene) and preferably kerosene bases that can be incorporated into the fuel pool and have high yields, starting from ethanol produced from a renewable source obtained from biomass that is also called bioethanol.

The process according to the invention that implements a scheme that comprises a stage for transformation of an aqueous bioethanol feedstock—produced starting from a renewable source that is obtained from biomass—into effluent that is for the most part ethylene followed by two oligomerization stages, with said two stages using specific catalytic systems, makes it possible to maximize the production of middle distillate bases and in particular kerosene, which constitutes both an asset for the refiner and an advantage from the standpoint of lasting development.

OBJECT OF THE INVENTION

This invention therefore describes a process for the production of middle distillate hydrocarbon bases and preferably a kerosene hydrocarbon base from an ethanol feedstock that is produced from a renewable source that is obtained from biomass, whereby said process comprises at least:

a) One stage for purification of said ethanol feedstock,
   b) One stage for dehydration of said purified ethanol feedstock that is obtained from stage a) into an effluent that is for the most part ethylene and that comprises water, whereby said stage works in the presence of an amorphous acid catalyst or a zeolitic acid catalyst,
   c) At least one stage for separation of the water that is present in said effluent that is for the most part ethylene, obtained from stage b),
   d) A first stage for oligomerization of at least a portion of the effluent that is for the most part ethylene obtained from stage c) in at least one olefinic effluent that comprises at least 80% by weight of olefins and that has four or more carbon atoms, in the presence of a homogeneous catalyst that comprises at least one bivalent nickel compound, whereby the percentages by weight are expressed in terms of percentages by weight relative to the total mass of the olefins that are contained in said olefinic effluent that is produced,
   e) A second stage for oligomerization of at least a portion of the effluent that is obtained from stage d), producing middle distillate hydrocarbon bases in the presence of an amorphous or zeolitic catalyst, whereby said zeolitic catalyst has at least pore openings that contain 10 or 12 oxygen atoms,
   f) A stage for fractionation of the effluent that is obtained from the oligomerization stage e).

DETAILED DESCRIPTION OF THE INVENTION

Feedstock

The feedstock that is treated in the process according to the invention is an ethanol feedstock that is produced from a renewable source that is obtained from biomass and that will consequently be called "bioethanol feedstock" in the description below.

Said bioethanol feedstock is a feedstock that is produced biologically, more specifically by fermentation of sugars obtained from, for example, sugar-producing crops such as sugarcane (saccharose, glucose, fructose, and sucrose), beet scraps, or else amylase plants (starch), or lignocellulosic biomass or hydrolyzed cellulose (glucose, for the most part, and xylose, galactose), containing variable quantities of water.

Said feedstock is advantageously obtained by fermentation from three sources: 1) sucrose from cane sugar or beet scraps, 2) the starch that is present in grains and tubers, and 3) the cellulose and the hemicellulose that are present in wood, grasses, and other lignocellulosic biomass, with starch, cellulose and hemicellulose having to be hydrolyzed into sugars before undergoing a fermentation stage.

The bioethanol feedstock that is used according to the invention therefore for the most part contains ethanol, at a level of more than 50% by weight and preferably more than 70% by weight, and it also advantageously contains a water content of greater than 2% by weight, preferably greater than 5% by weight, and in a preferred manner greater than 10% by weight, a content of cationic impurity such as, for example, the ions $Na^+$, $Ca^{2+}$, $Mn^{2+}$, $Fe^{2+}$, $Cu^{2+}$, and $Zn^{2+}$, that is advantageously less than 0.5% by weight, a content of anionic impurity, such as, for example, the ions of $Cl^-$, sulfate, nitrite, nitrate, phosphates, that is advantageously less than 0.5% by weight, a content of other alcohols, such as, for example, methanol or butanol, that is advantageously less than 10% by weight, and preferably less than 5% by weight, a content of oxidized compounds other than the alcohols, such as, for example, ethers, acids, ketones, aldehydes and/or esters, that is advantageously less than 1% by weight, and a nitrogen and sulfur content that is advantageously less than 0.5% by weight, whereby the percentages by weight are expressed relative to the total mass of said feedstock.

In accordance with stage a) of the process according to the invention, the feedstock undergoes a purification stage in such a way as to eliminate the cationic and anionic impurities as well as at least a portion of the oxidized compounds to limit the deactivation of the catalyst for dehydration that is placed downstream.

The purification stage is advantageously implemented by means that are known to one skilled in the art, such as, for example, the use of at least one resin, the adsorption of impurities and oxidized compounds on solids selected from among the molecular sieves, active carbon, alumina and zeolites, and distillation for producing a purified bioethanol fraction and a fraction that comprises the organic impurities so as to obtain a purified feedstock that responds to the level of impurities compatible with the dehydration catalyst.

A pretreatment stage can advantageously be implemented by hydrogenation of oxidized unsaturated compounds in the presence of a nickel-based catalyst, whereby said pretreatment stage is implemented before or after the purification stage and preferably after.

In accordance with stage b) of the process according to the invention, the purified ethanol feedstock that is obtained from stage a) undergoes a stage for dehydration into an effluent that is for the most part ethylene and that comprises water, whereby said stage works in the presence of a dehydration catalyst that is known to one skilled in the art, in particular an amorphous acid catalyst or a zeolitic acid catalyst.

In the case where the catalyst that is used in dehydration stage b) is a zeolitic catalyst, said catalyst that comprises at least one zeolite that is selected from among the zeolites and that has at least pore openings that contain 10 or 12 oxygen atoms (10 MR or 12 MR) [sic]. It is actually known to define the size of the pores of the zeolites by the number of oxygen atoms that form the annular section of the channels of the zeolites, called "member ring" or MR in English. In a preferred manner, said zeolitic catalyst comprises at least one zeolite that has a structural type that is selected from among the structural types MFI, FAU, MOR, FER, and BEA.

The zeolite that is employed in the catalyst that is used in stage b) of the process according to the invention can advantageously be modified by dealuminification or desilication according to any dealuminification or desilication method that is known to one skilled in the art.

In the case where the catalyst that is used in dehydration stage b) is an amorphous acid catalyst, said catalyst comprises at least one porous refractory oxide that is selected from among alumina, alumina that is activated by a mineral acid deposit and silica alumina.

Said amorphous or zeolitic dehydration catalyst that is used in stage b) of the process according to the invention can also advantageously comprise at least one oxide-type matrix that is also called a binder. Matrix, according to the invention, is defined as an amorphous or poorly crystallized matrix.

Said matrix is advantageously selected from among the elements of the group that is formed by clays (such as, for example, among the natural clays such as kaolin or bentonite), magnesia, aluminas, silicas, silica-aluminas, aluminates, titanium oxide, boron oxide, zirconia, aluminum phosphates, titanium phosphates, zirconium phosphates, and carbon. Preferably, said matrix is selected from among the elements of the group that is formed by aluminas, silicas, and clays.

In a preferred embodiment, the binder has a macroporous texture as described in the patent US2009/088595.

The catalyst for dehydration that is used in stage b) of the process according to the invention is advantageously shaped in the form of grains of different shapes and sizes. It is advantageously used in the form of cylindrical or multilobed extrudates such as bilobed, trilobed, or multilobed extrudates of straight or twisted shape, but it can optionally be produced and used in the form of crushed powder, tablets, rings, balls, wheels, or spheres. Preferably, said catalyst is in the form of extrudates or balls.

Dehydration stage b) of the process according to the invention advantageously works at a temperature of between 250 and 600° C., preferably between 300 and 600° C., and in a preferred manner between 300 and 500° C., at an absolute pressure of between 0.1 and 5 MPa, preferably between 0.1 and 2.5 MPa, and in a preferred manner between 0.1 and 1 MPa, and at an hourly speed by weight of between 0.1 and 50 $h^{-1}$, and preferably between 0.5 and 15 $h^{-1}$. The hourly speed by weight is defined as being the ratio of the mass flow rate of the feedstock to the catalyst mass.

In stage b) of the process according to the invention, the catalysts that are used and the operating conditions are selected in such a way as to maximize the production of ethylene. The dehydration reaction implemented in stage b) of the process according to the invention is as follows:

$$2C_2H_5OH \rightarrow 2CH_2=CH_2 + 2H_2O$$

Said stage b) produces an effluent that is for the most part ethylene. An effluent that is for the most part ethylene, produced during stage b), is defined as an effluent that comprises at least 95%, preferably at least 97%, and in a preferred manner at least 98% by weight of ethylene relative to the total mass of the carbon compounds that are formed and present in said effluent that is produced in said stage b). In addition to the majority presence of ethylene, said carbon effluent can also comprise other hydrocarbon, hydroxycarbon or carbon compounds in a very minority proportion. In particular, said carbon effluent advantageously comprises less than 5%, preferably less than 3%, and in a preferred manner less than 2% by weight of compounds that have three or more carbon atoms and oxidized compounds, such as, for example, CO2, CO, diethyl ether or acetaldehyde, whereby the percentages are expressed in terms of percentages by weight relative to the total mass of the carbon compounds that are formed and present in said effluent that is produced in said stage b).

The conversion of the bioethanol feedstock in stage b) is advantageously greater than 90%, preferably 95%, and in a preferred manner greater than 98%.

Conversion of the bioethanol feedstock is defined as the ratio of the difference between the mass flow rate of the ethanol feedstock ($C_2H_5OH$) at the input and the mass flow rate of the ethanol feedstock ($C_2H_5OH$) at the output of stage b) to the mass flow rate of the ethanol feedstock at the input.

The transformation of the feedstock is accompanied by the deactivation of the catalyst by coking and/or by adsorption of inhibiting compounds. The catalyst should therefore periodically undergo a regeneration stage described below.

A water-based or paraffin-based diluent that is obtained from a feedstock that is external to the process according to the invention, such as, for example, paraffins that have a carbon number of between two and eight, can advantageously be added to the bioethanol feedstock after purification in a diluent to feedstock molar ratio of advantageously between 0.5 to 20 for the purpose of stabilizing the catalyst of stage b) of the process according to the invention.

Stage b) of the process according to the invention for dehydration of said purified feedstock into an effluent that is for the most part ethylene is advantageously implemented in at least one fixed-bed reactor, for example according to the teaching of the U.S. Pat. No. 4,396,789, or in a moving-bed or fluidized-bed reactor.

In the case where stage b) is implemented in a fluidized bed, the catalyst will assume the shape of balls, of a size that is advantageously less than 500 microns and preferably less than 300 microns.

In the case where stage b) is implemented in a fixed bed, the regeneration of the catalyst that is used in said stage b) is advantageously carried out by oxidation of coke and inhibiting compounds under a stream of air, for example by using a recirculation of the combustion air with or without water so as to dilute the oxygen and control the regeneration exothermy. In this case, it is advantageously possible to adjust the oxygen content at the input of the reactor by a supply of air. The regeneration takes place at a pressure between the atmospheric pressure (0 bar, relative) and the reaction pressure. The regeneration temperature is advantageously selected between 400 and 600° C.; it can advantageously vary during regeneration. The end of the regeneration is detected when there is no longer oxygen consumption, sign of a total combustion of the coke.

In the case where stage b) is implemented in a moving or fluidized bed as described in the U.S. Pat. No. 4,134,926, the regeneration of the catalyst is carried out continuously.

In accordance with stage c) of the process according to the invention, the effluent that is for the most part ethylene that is obtained from stage b) undergoes at least one stage for separation of the water that is present in the effluent that is produced during stage b).

Preferably, said effluent that is obtained from stage b) undergoes at least one stage for separation of the water that is present in said effluent, whereby said separation stage is followed by at least one stage for purification of said effluent previously separated from water. Said stage c) of the process according to the invention makes it possible to eliminate the impurities that are harmful for the oligomerization catalysts that are used for the implementation of stages d) and e) placed downstream, and in particular said stage c) allows the elimination of the oxidized compounds that are present in said effluent.

Stage c) of the process according to the invention that implements at least one stage for separation of water and/or optionally at least one stage for purification of said effluent that is for the most part ethylene, obtained from said stage b), can advantageously be implemented by any method that is known to one skilled in the art, such as, for example, the successive combination of a treatment in a column for washing with water, and then passage in a column for absorption with MDEA (methyldiethylamine) or another amine and in a column for washing with soda or any other means that is known to one skilled in the art. Driers can advantageously be used in such a way as to reach a water content that is compatible with the oligomerization catalysts that are used downstream in oligomerization stages d) and e). The water content of the effluent that is sent into the oligomerization stage d) is advantageously between 0 and 500 ppm and preferably less than 100 ppm.

At least a portion of the aqueous effluent that is eliminated during stage c) is advantageously recycled upstream from stage b) for dehydration of said purified feedstock, serving as a diluent of the purified bioethanol feedstock.

In accordance with stage d) of the process according to the invention, the effluent that is for the most part ethylene and is obtained from separation stage c) is sent into a first oligomerization stage d) in which said effluent that is for the most part ethylene is oligomerized in the presence of a homogeneous catalyst that comprises at least one bivalent nickel compound, in at least one olefinic effluent that comprises at least 80% by weight and preferably at least 90% by weight of olefins having four or more carbon atoms, whereby the percentages by weight are expressed relative to the total mass of the olefins contained in said olefinic effluent that is produced.

At least a portion, i.e., at least 50% by weight, preferably at least 90% by weight, of said effluent that is obtained from said stage c), and in a preferred manner all of said effluent that is obtained from said stage c), is subjected to said first oligomerization stage.

In addition to the majority presence of olefins that have four or more carbon atoms, the olefinic effluent that is produced during the first oligomerization stage d) also advantageously comprises less than 20%, preferably less than 10%, by weight of ethylene (C2) that has not reacted during the first oligomerization stage d), whereby the percentages are expressed in terms of percentages by weight relative to the total mass of the olefins contained in the effluent that is produced.

The objective of said first oligomerization stage d) is to obtain an olefinic hydrocarbon effluent that has four or more carbon atoms and, in particular, that is rich in olefins and has between four and eight carbon atoms.

The first oligomerization stage d) leads to the production of an olefinic effluent that comprises at least 80% by weight relative to the total mass of olefins contained in said olefinic effluent, with olefins that have four or more carbon atoms. In particular, said effluent is rich in olefinic hydrocarbons having between four and eight carbon atoms and also comprises olefinic hydrocarbons having at least nine carbon atoms (C9+). More particularly, said olefinic effluent that is produced during the first oligomerization stage d) advantageously comprises at least 80% by weight, preferably at least 90% by weight, of olefinic compounds having for the most part between four and eight carbon atoms and less than 20% by weight and preferably less than 10% by weight of olefinic compounds that for the most part have nine or more carbon atoms, whereby the percentages by weight are expressed relative to the total mass of the olefins contained in said olefinic effluent that is produced.

Preferably, the feedstock that enters into the reactor(s) implementing said first oligomerization stage d) is introduced therein mixed with a portion, preferably all, of a light olefinic, hydrocarbon-containing effluent that for the most part has between two and four carbon atoms (C2-C4 light olefinic effluent), which is obtained from an optional separation stage that is described below and preferably implemented between said oligomerization stages d) and e) according to the invention.

In accordance with stage d) of the process according to the invention, the catalyst that is used in the first oligomerization stage d) is a homogenous catalyst that comprises at least one bivalent nickel compound, i.e., the catalyst is soluble in the liquid phase that consists of dissolved ethylene and its oligomerization products.

Concerning an implementation by homogeneous catalysis, one skilled in the art can usefully refer to the teaching of U.S. Pat. Nos. 7,235,703 and 4,362,650.

The homogeneous catalyst that is used in oligomerization stage d) of the process according to the invention comprises at least one bivalent nickel compound, optionally at least one hydrocarbyl-aluminum halide, and optionally at least one Brönsted organic acid. Preferably, the catalyst can also contain at least one carboxylic acid anhydride.

The bivalent nickel compounds are preferably soluble compounds with more than one gram per liter of hydrocarbon medium and more particularly in the reagents and the reaction medium and in a preferred manner, nickel carboxylates with general formula $(RCOO)_2Ni$ where R is a hydrocarbyl radical, for example alkyl, cycloalkyl, alkenyl, aryl, aralkyl or alkaryl containing up to 20 carbon atoms, and preferably a hydrocarbyl radical with 5 to 20 carbon atoms. The radical R can be substituted by one or more halogen atoms, by one or more hydroxy, ketone, nitro, or cyano groups, or other groups that do not interfere with the reaction. The two radicals R can also constitute an alkylene radical with 6 to 18 carbon atoms.

The bivalent nickel compounds are advantageously selected from among the following bivalent nickel salts: octoate, ethyl-2-hexanoate, decanoate, stearate, oleate, salicylate and hydroxydecanoate, taken by themselves or in a mixture, and preferably the bivalent nickel compound is nickel ethyl-2-hexanoate.

The hydrocarbyl-aluminum halides are preferably hydrocarbyl-aluminum dihalides corresponding to the formula $AlRX_2$, in which R is a hydrocarbyl radical and X is a halogen that is selected from among fluorine, chlorine, bromine and iodine, taken by themselves or in a mixture. The hydrocarbyl-aluminum halides are advantageously selected from among dichloroethylaluminum, dichloroisobutylaluminum and dibromoethylaluminum. These hydrocarbylaluminum dihalides can advantageously be enriched with aluminum trihalides ($AlX_3$), such as, for example, aluminum trichloride.

The Brönsted organic acid compounds preferably correspond to the formula HY, where Y is an organic anion, for example carboxylic, sulfonic or phenolic. Said compounds preferably have a pKa at 20° C. that is at most equal to 3 and are selected preferably from the group that is formed by the halogenocarboxylic acids of formula RCOOH in which R is a halogenated alkyl radical and preferably a halogenated alkyl radical that contains at least one alpha-halogen atom of the group —COOH with a total of two to ten carbon atoms.

Preferably, a halogenoacetic acid of formula $CX_pH_{3-p}$—COOH is used in which X is fluorine, chlorine, bromine or iodine, with p an integer from 1 to 3. By way of example, it is possible to cite trifluoroacetic, difluoroacetic, fluoroacetic, trichloroacetic, dichloroacetic, and chloroacetic acids. These examples are not limiting, and it is also possible to use arylsulfonic, alkylsulfonic, or fluoroalkylsulfonic acids, or picric acid or nitroacetic acid.

The catalyst that is used in the first oligomerization stage d) can also contain at least one carboxylic acid anhydride of formula $(RCO)_2O$ in which R is a hydrocarbyl radical that can advantageously contain one or more halogen atoms. The carboxylic acid anhydrides are advantageously selected from among the following anhydrides: octoic, ethyl-2-hexanoic, decanoic, stearic, oleic, trifluoroacetic, monofluoroacetic, trichloroacetic, monochloroacetic, pentafluoropropionic, or heptafluorobutyric, taken by themselves or in a mixture. Preferably, carboxylic acid anhydride is the anhydride of trifluoroacetic acid.

The different compounds that constitute the catalyst can be mixed in any order. However, it is preferable first to mix the nickel compound with the Brönsted organic acid, and next to introduce the aluminum compound.

A preconditioning of the catalyst can be carried out before bringing the catalyst into contact with the ethylene. The preconditioning of the catalytic composition consists in carrying out the mixing of three components in a hydrocarbon solvent, for example an alkane or an aromatic hydrocarbon, or else a halogenated hydrocarbon, or else, in a preferred way, the olefins that are produced in the oligomerization reaction, while being stirred and under inert atmosphere, for example, under nitrogen or under argon, at a controlled temperature of between 0 and 80° C., preferably between 10 and 60° C., for a duration of 1 minute to 5 hours, preferably 5 minutes to 1 hour. The thus obtained solution is next transferred under inert atmosphere into the oligomerization reactor.

This preconditioning of the catalyst makes it possible to increase the activity for the catalyst in the oligomerization of the ethylene.

The catalyst that is present in said unit that works the oligomerization stage d) comes in liquid form. Based on the chemical composition of said catalyst, the proportions by weight of each of the components of the catalyst can be monitored during the synthesis of the catalyst. The molar ratio of the hydrocarbylaluminum halide to the nickel compound, expressed by the Al/Ni ratio, is 2/1 to 50/1, and preferably 2/1 to 20/1.

The molar ratio of the Brönsted acid to the nickel compound is 0.25/1 to 10/1, and preferably 0.25/1 to 5/1. If the catalyst comprises carboxylic acid anhydride, the molar ratio of the carboxylic acid anhydride to the nickel compound is advantageously between 0.001/1 and 1/1, very advantageously between 0.01/1 and 0.5/1.

The first oligomerization stage d) implemented by homogeneous catalysis is advantageously carried out continuously: The catalytic solution is injected into the unit that works the oligomerization stage, and the ethylene is injected therein continuously. The unit that works said stage for oligomerization of the ethylene by homogeneous catalysis comprises one or more reactors of the perfectly stirred type, in series, with recycling of at least a portion of the effluent of the reactor in the reactor, whereby this recycling has been advantageously cooled. The recycling has a thermal diluent and heat extractor role because the reaction is exothermic. The recycling is inside the oligomerization unit.

The first oligomerization stage d) can be implemented in a reactor with one or more reaction stages in a series, whereby the feedstock that is for the most part ethylene and/or the previously preconditioned catalytic composition are introduced continuously, either in the first stage or in the first stage and any other of the stages.

The operating conditions in the reactor(s) working the oligomerization stage by homogeneous catalysis are such that the temperature is between −20° C. and +80° C., and the pressure is adequate for allowing the existence of a liquid phase in the reactor(s). In a preferred manner, the absolute total pressure in the reactor(s) is between 2 and 8 MPa.

Said olefinic effluent that is obtained from said first oligomerization stage d) preferably comprises at least 80% by weight and preferably at least 90% by weight of olefinic compounds having four or more carbon atoms and less than 20% by weight and preferably less than 10% by weight of ethylene (C2) that has not reacted during the first oligomerization stage d), whereby the percentages are expressed in percentages by weight relative to the total mass of the olefins that are contained in said olefinic effluent that is produced.

At the output of the first oligomerization stage d), the homogeneous catalytic system is found mixed with the olefinic effluent that is produced during stage d) and the ethylene that has not reacted.

In a first embodiment, at least a portion, and preferably all, of said olefinic effluent that is produced during the first oligomerization stage d) is sent directly into the second oligomerization stage e).

In a second embodiment, said olefinic effluent, produced during the first oligomerization stage d), undergoes at least one stage for treatment of the homogeneous catalytic system and/or at least one stage for optional separation of said effluent before being sent into the second oligomerization stage e).

In said second embodiment, stage for treatment of the homogeneous catalytic system is defined as a stage in which said catalytic system is deactivated and separated from the homogeneous reaction medium and in particular from the olefinic effluent that is obtained from the first oligomerization stage d).

Said stage for optional treatment of the homogeneous catalytic system is advantageously implemented according to three methods:
1) Either by the use of collection mass,
2) Or by treatment by a base and/or an acid of the olefinic effluent that is obtained from the first oligomerization stage d), which may or may not be neutralized by a base,
3) Or by the separation of said olefinic effluent that is obtained from the first oligomerization stage d), neutralized or not by a base, into a first effluent that comprises at least a portion of C9+ olefinic compounds and also the homogeneous catalytic system and into a second olefinic effluent that is free of the catalytic system, whereby said separation is followed by treatment of the effluent that comprises at least a portion of the C9+ olefinic compounds and the homogeneous catalytic system by acid and/or basic washing or by the use of collection mass.

In the case where said stage for treatment of the homogeneous catalytic system is advantageously implemented by the use of collection mass, said collection masses are advantageously selected from among aluminas, silicas and activated earths, taken by themselves or in a mixture, whereby the homogeneous catalytic system adsorbs on the surface of the solid that constitutes the collection mass.

In the case where said stage for treatment of the homogeneous catalytic system is advantageously implemented by treatment of said olefinic effluent, containing said homogeneous catalytic system, by a base and/or an acid, said treatment advantageously consists of an addition of an aqueous solution that will make possible the transfer of the catalytic system from the hydrocarbon phase to the aqueous phase. The catalytic system is eliminated from the hydrocarbon phase by separation of the aqueous phase and the hydrocarbon phase, which are immiscible. The treatment by a base and/or an acid is advantageously done successively using ammonia and/or an aqueous solution of soda and/or an aqueous solution of sulfuric acid.

The treatment by acid and/or basic washing is advantageously followed by a stage for drying said effluent, whereby said drying stage is preferably implemented by using molecular sieves or adsorbents whose purpose is the residual elimination of water.

In the case where said stage for treatment of the homogeneous catalytic system is advantageously implemented according to the third method, the separation of said olefinic effluent into a first effluent that comprises at least a portion of the C9+ compounds and also the homogeneous catalytic system and into a second olefinic effluent that is free of the catalytic system is advantageously implemented by any method that is known to one skilled in the art, such as, for example, the combination of one or more high- and/or low-pressure and high- and/or low-temperature separator tanks and/or distillation stages comprising one or more distillation columns, and preferably by the combination of one or more high- and/or low-pressure and high- and/or low-temperature separator tanks.

According to the third method, said separation is then advantageously followed by the treatment of said effluent that comprises at least a portion of the C9+ compounds and the homogeneous catalytic system by acid and/or basic washing or by the use of a collection mass as defined above.

In the case where the treatment is implemented by acid and/or basic washing, it is advantageously followed by a stage for drying the effluent comprising at least a portion of the C9+ compounds, whereby said drying stage is preferably implemented by the use of molecular sieves or adsorbents whose purpose is the residual elimination of water.

In said second embodiment, at least one stage for operational separation of the olefinic effluent produced during the first oligomerization stage d), whereby said effluent optionally has undergone a stage for treatment of the homogeneous catalytic system, is advantageously implemented between the first oligomerization stage d) and the second oligomerization stage e). Preferably, at least one optional separation stage is implemented between said stage for treatment of the homogeneous catalytic system, when the latter is implemented, and the second oligomerization stage e). This stage makes possible the separation of said olefinic effluent that is obtained from the first oligomerization stage d) or obtained from the treatment stage of the homogeneous catalytic system into at least one olefinic effluent having four or more carbon atoms and into at least one light olefinic effluent (C2-C4).

In particular, said olefinic effluent that has four or more carbon atoms is rich in olefinic compounds that have between four and eight carbon atoms and also comprises olefinic compounds that have at least nine carbon atoms (C9+).

Said separation stage can advantageously be implemented by any method that is known to one skilled in the art, such as, for example, the combination of one or more high- and/or low-pressure and high- and/or low-temperature separator tanks, and/or distillation stages that comprise one or more distillation columns.

C2-C4 light olefinic effluent is defined as an effluent that advantageously comprises at least 50% by weight and preferably at least 65% by weight of olefinic compounds that have between two and four carbon atoms and that also advantageously comprises less than 50% by weight and preferably less than 45% by weight of olefinic compounds that have five or more carbon atoms, whereby the percentages by weight are expressed relative to the total mass of olefins of said C2-C4 light olefinic effluent that is obtained from the optional separation.

Preferably, all of said C2-C4 light olefinic effluent is recycled in the first oligomerization stage d).

Olefinic effluent is defined as having four or more carbon atoms, an effluent that advantageously comprises at least 80% by weight, preferably at least 90% by weight, of olefinic compounds that have between four and eight carbon atoms (C4-C8) and less than 20% by weight and preferably less than 10% by weight, of olefinic compounds that have more than nine carbon atoms (C9+), whereby the percentages by weight are expressed relative to the total mass of olefins that are present in said olefinic effluent that has four or more carbon atoms.

In said second embodiment and in the case where the stage for treatment of the homogeneous catalytic system is implemented by the use of collection mass or by acid and/or basic washing, the olefinic effluent that is obtained from said stage for treatment of the homogeneous catalytic system can advantageously either be sent directly into the second oligomerization stage e), without undergoing an optional intermediate separation stage, or can undergo an optional separation stage in which said effluent is advantageously separated into at least one olefinic effluent that has four or more carbon atoms and into at least one light olefinic effluent (C2-C4).

In the case where the olefinic effluent that is obtained from said stage for treatment of the homogeneous catalytic system undergoes said optional separation stage, all of said C2-C4 light olefinic effluent that is obtained from said separation stage is preferably recycled in the first oligomerization stage d).

Said olefinic effluent that has four or more carbon atoms and said light olefinic effluent (C2-C4) have the meaning defined above.

According to a first variant, in the case where the olefinic effluent that is obtained from said stage for treatment of the homogeneous catalytic system undergoes said optional separation stage, all of the C4+ olefinic effluent that is obtained from said separation stage, comprising the C4-C8 olefinic compounds and the C9+ olefinic compounds, is advantageously sent into the second oligomerization stage e).

According to a second variant, the C4+ olefinic effluent is advantageously separated, in a second optional separation stage, into at least one olefinic effluent that has between four and eight carbon atoms (C4-C8) and at least one olefinic effluent that has more than nine carbon atoms (C9+).

In this case, said C4-C8 olefinic effluent is advantageously sent into the second oligomerization stage e), and said C9+ olefinic effluent is advantageously sent directly into stage f) for final fractionation.

Said C4-C8 olefinic effluent is defined as being an effluent that comprises olefinic compounds that are distributed according to the following distribution: at least 50% by weight and preferably at least 70% by weight of olefinic compounds having between four and eight carbon atoms and less than 50% by weight and preferably less than 30% by weight of other olefinic compounds, whereby the percentages by weight are expressed relative to the total mass of the olefins that are present in the C4+ olefinic effluent.

In the same manner, said C9+ olefinic effluent is defined as being an effluent that comprises olefinic compounds that are distributed according to the following distribution: at least 50% by weight and preferably at least 70% by weight, of olefinic compounds that have nine or more carbon atoms and that also advantageously comprise less than 50% by weight and preferably less than 30% by weight of compounds that have fewer than nine carbon atoms, whereby the percentages by weight are expressed relative to the total mass of the olefins that are present in the C4+ olefinic effluent.

In said second embodiment and in the case where the stage for treatment of the homogeneous catalytic system is implemented according to Method 3 described above, said separation produces a first effluent that comprises at least a portion of the C9+ olefinic compounds and also the homogeneous catalytic system and a second olefinic effluent that is free of the catalytic system. Said separation is then followed by treatment of the effluent that comprises at least a portion of the C9+ compounds and the homogeneous catalytic system by acid and/or basic washing or by the use of collection mass. Said olefinic effluent that comprises at least a portion of the C9+ compounds, separated from the homogeneous catalytic system at the end of the acid and/or basic washing, is preferably dried before being sent into stage f) for final fractionation.

In this case, said olefinic effluent that is free of the catalytic system preferably comprises at least 80% by weight and preferably at least 90% by weight of C4+ olefinic compounds and less than 20% by weight and preferably less than 10% by weight of ethylene (C2) that has not reacted during the first oligomerization stage d), whereby the percentages are expressed in percentages by weight relative to the total mass of the olefins that are contained in said olefinic effluent that is free of the catalytic system.

Preferably, said C4+ olefinic compounds advantageously comprise at least 80% by weight, preferably at least 90% by weight, of C4-C8 olefinic compounds and less than 20% by weight and preferably less than 10% by weight of C9+ olefinic compounds, whereby the percentages by weight are expressed relative to the total mass of olefins that are present in said C4+ olefinic effluent.

According to a first variant, said olefinic effluent that is free of the catalytic system that is obtained from the separation stage is advantageously sent directly into the second oligomerization stage e), without an optional second intermediate separation stage.

According to a second variant, said olefinic effluent that is free of the catalytic system that is obtained from the separation stage next advantageously undergoes a second optional separation stage in which said effluent is advantageously separated into at least one C4+ effluent and at least one light olefinic effluent (C2-C4).

Preferably, all of said C2-C4 light olefinic effluent is recycled in the first oligomerization stage d).

Thus, the feedstock that is sent into the input of the second oligomerization stage e) advantageously comprises either:

All of the effluent that is obtained from the first oligomerization stage d) in the case where no stage for treatment of the homogeneous catalytic system and/or optional separation is implemented between the first and the second oligomerization stage, Or at least a portion of the effluent that is obtained from the first oligomerization stage d), separated from all of said light olefinic effluent (C2-C4) and/or all of said C9+ olefinic effluent, in the case where at least one stage for optional treatment of the homogeneous catalytic system and/or for optional separation are implemented between the first and the second oligomerization stages.

At least a portion of the gasoline fraction that is obtained from the final fractionation stage f) can advantageously also be recycled in the second oligomerization stage e) of the process according to the invention and mixed with the feedstock of stage e).

In accordance with stage e) of the process according to the invention, at least a portion of the effluent that is obtained from the first oligomerization stage d), optionally separated from all of said light olefinic effluent (C2-C4) and/or all of the C9+ olefinic effluent, undergoes a second oligomerization stage e) in the presence of an amorphous or zeolitic catalyst, whereby said zeolitic catalyst has at least pore openings that contain 10 or 12 oxygen atoms (10 MR or 12 MR) for producing middle distillate hydrocarbon bases.

According to the invention, the second oligomerization stage e) works in the presence of an amorphous catalyst or comprises at least one zeolite that has at least pore openings that contain 10 or 12 oxygen atoms (10 MR or 12 MR) and is advantageously selected from among aluminosilicate-type zeolites that have an overall Si/Al ratio that is greater than 10.

According to a preferred embodiment, the catalyst that is used in the second oligomerization stage e) is an amorphous catalyst that comprises and preferably consists of an amorphous mineral material that is selected from among the silica-aluminas and siliceous aluminas and in a preferred manner, the silica aluminas.

According to another preferred embodiment, said catalyst that is used in the second oligomerization stage e) comprises at least one zeolite that is selected from among the aluminosilicate-type zeolites that have an overall Si/Al ratio that is greater than 10 and a 10 or 12 MR pore structure, preferably selected from among the following zeolites: ZSM-5, ZSM-12, NU-86, mordenite, ZSM-22, NU-10, ZBM-30, ZSM-48, ZSM-11, ZSM-57, IZM-2, ITQ-6 and IM-5, taken by themselves or in a mixture, preferably from among the zeolites ZSM-5, NU-10 and ZBM-30, taken by themselves or in a mixture; in a very preferred manner, the zeolite is ZBM-30, and in an even more preferred manner, the zeolite is ZBM-30 that is synthesized in the presence of the triethylenetetramine structuring agent.

The zeolite that is employed in the catalyst that is used in stage e) of the process according to the invention can advantageously undergo several post-treatments that are known to one skilled in the art, such that, for example, it can be modified by dealuminification or desilication according to any method of dealuminification, external surface passivation or desilication known to one skilled in the art, for the purpose of improving its activity and/or its stability.

Said catalyst that is used in stage e) of the process according to the invention also advantageously comprises at least one oxide-type matrix that is also called a binder. Matrix, according to the invention, is defined as an amorphous or poorly crystallized matrix.

Said matrix is advantageously selected from among the elements of the group that is formed by clays (such as, for example, from among natural clays such as kaolin or bentonite), magnesia, aluminas, silicas, silica-aluminas, aluminates, titanium oxide, boron oxide, zirconia, aluminum phosphates, titanium phosphates, zirconium phosphates, and carbon. Preferably, said matrix is selected from among the elements of the group that is formed by aluminas, clays and silicas; in a more preferred manner, said matrix is selected from among aluminas, and in an even more preferred manner, said matrix is gamma-alumina.

The catalysts that are used in stage e) of the process according to the invention are advantageously shaped in the form of grains of different shapes and sizes. They are advantageously used in the form of cylindrical or polylobed extrudates, such as bilobed, trilobed, or polylobed extrudates of straight or twisted shape, but they can optionally be produced and used in the form of crushed powder, tablets, rings, balls, wheels, and spheres. Preferably, said catalysts are in the form of extrudates with a size of between 1 and 10 mm.

The second oligomerization stage e) is advantageously implemented in at least one fixed-bed reactor.

The second stage e) of the process according to the invention advantageously works at a temperature of between 50 and 400° C., preferably between 100 and 350° C., and in a preferred manner between 100 and 300° C., at an absolute pressure of between 2 and 15 MPa, preferably between 2 and 8 MPa, and in a preferred manner between 3 and 8 MPa, and at an hourly speed by weight of between 0.1 and 10 $h^{-1}$, and preferably between 0.4 and 5 $h^{-1}$.

In accordance with the invention, middle distillate hydrocarbon bases (gas oil and/or kerosene) are produced at the end of the second oligomerization stage e).

The olefinic hydrocarbon effluent that comprises the middle distillate hydrocarbon bases produced during the second oligomerization stage e) is an olefinic effluent that comprises at least 80% by weight and preferably at least 90% by weight of a C4+ olefinic effluent and less than 20%, preferably less than 10% ethylene (C2) that has not reacted, whereby the percentages by weight are expressed relative to the total mass of the olefins that are contained in the effluent that is produced.

Said C4+ olefinic compounds advantageously comprise less than 50% by weight and preferably less than 40% by weight of C4-C8 olefinic compounds, and at least 50% by weight and preferably at least 60% by weight of C9+ olefinic compounds, whereby the percentages by weight are expressed relative to the total mass of said C4+ olefinic compounds.

The second oligomerization stage e) therefore makes possible the production of an olefin-enriched effluent having nine or more carbon atoms, by the conversion of olefinic compounds (C4-C8) entering into said stage in these heavier compounds.

The process according to the invention is a flexible process in this sense that the operating conditions and the selection of the catalyst in the second oligomerization stage e) make it possible to orient the reaction to one or the other of the target products, namely in one case to the majority production of a gas-oil-type hydrocarbon base and in the other a kerosene-type hydrocarbon base.

In the case where the majority production of gas-oil-type hydrocarbon base is more particularly desired, the second oligomerization stage e) advantageously works in the presence of a catalyst that comprises at least one zeolite that is selected from among the aluminosilicate-type zeolites that have an overall Si/Al ratio that is greater than 10 and a 10 or 12 MR pore structure, and at a temperature of between 200 and 300° C., at a pressure of between 3 and 7 MPa, and at an hourly speed by weight of between 0.1 and 5 $h^{-1}$.

In the case where the majority production of kerosene-type hydrocarbon base is more particularly desired, the second oligomerization stage e) advantageously works in the presence of an amorphous catalyst, preferably comprising and in a preferred manner consisting of silica alumina at a temperature of between 100 and 300° C., at a pressure of between 2 and 6 MPa, and at an hourly speed by weight of between 0.1 and 5 $h^{-1}$.

In accordance with the invention, the effluent that is obtained from the second oligomerization stage e) comprising the middle distillate hydrocarbon bases undergoes a final fractionation stage f) in at least one distillation column in such a way as to separate said bases into at least two fractions that correspond to the gasoline fractions and middle distillates (gas oil and/or kerosene). A light effluent that comprises the C2 to C4 compounds can also be separated to be upgraded in pure form or in a mixture. A heavy fraction that has an initial boiling point of between 350 and 370° C. can also be advantageously separated. These cited products are in no way restrictive.

At least a portion of said light effluent that comprises the C2 to C4 compounds obtained from fractionation stage f) can advantageously be recycled in the first oligomerization stage d) of the process according to the invention.

At least a portion of the gasoline fraction obtained from the final fractionation stage f) can advantageously be recycled in the second oligomerization stage e) of the process according to the invention.

One of the objectives of this invention is to maximize the yield of middle distillate bases, and preferably kerosene base, whereby said light effluent and the gasoline fraction, which are undesirable, are thus again oligomerized respectively in stage d) and in stage e) of the process according to the invention, making possible the increase of their molecular weight and thus the increase of their boiling point and their compatibility with the desired use.

At least a portion, and preferably all, of the middle distillate base (gas oil and/or kerosene) obtained from the final fractionation stage f) advantageously undergoes a stage for hydrogenation of the olefins that are produced, for the purpose of allowing their incorporation into the fuel pool.

Preferably, at least a portion, and preferably all, of the middle distillate base (gas oil and/or kerosene), obtained from the final fractionation stage f), is brought into contact with a hydrogen-rich gas in the presence of a catalyst that comprises at least one metal from group VIII, advantageously selected from among palladium and nickel, taken by itself or in a mixture, and a substrate that is advantageously selected from among alumina, silica, or silica-alumina.

The catalyst that is employed in the optional hydrogenation stage comprises a palladium content that is advantageously encompassed between 0.1 and 10% by weight and/or a content of nickel, advantageously between 1 and 60% by weight relative to the total mass of the catalyst.

The optional hydrogenation stage advantageously works at a temperature of between 100 and 250° C. at the input of the reactor, at a pressure of between 2 and 5 MPa, and at an hourly speed by weight that is between 0.05 and 8 h–1.

The performance of the hydrogenation is validated by measuring the bromine number, which is advantageously at most 5 g of Br/100 g, in the case where it is desired to saturate all of the unsaturated compounds that are present in the fraction that is to be hydrogenated.

The effluent that is obtained from the optional hydrogenation stage for the most part contains hydrocarbons that can be upgraded and incorporated in the kerosene and/or gas oil pool, and preferably kerosene.

According to one embodiment, at least a portion of said effluent that is obtained from the optional hydrogenation stage can advantageously be recycled either in the first oligomerization stage d) in such a way as to constitute a diluent of the feedstock and to thus stabilize the catalyst and/or can advantageously be introduced at the optional separation stage in such a way as to improve the separation.

An optional separation stage that follows the hydrogenation stage is advantageously implemented for allowing the fractionation into a kerosene fraction and/or a gas oil fraction and/or a fraction that has a boiling point that is greater than 360° C.

BRIEF DESCRIPTION OF THE FIGURES

FIG. 2 diagrammatically shows the process for production of middle distillate bases from bioethanol of this invention in a particular embodiment that includes a stage for treatment of the homogeneous catalytic system by acid and/or basic washing, followed by a separation stage, between the first and second oligomerization stages d) and e).

In FIG. 1, the ethanol feedstock that is produced from a renewable source obtained from the biomass, called bioethanol, is introduced into a reaction zone (A) via the pipe (1) in which said feedstock undergoes a purification stage.

Figure 1:
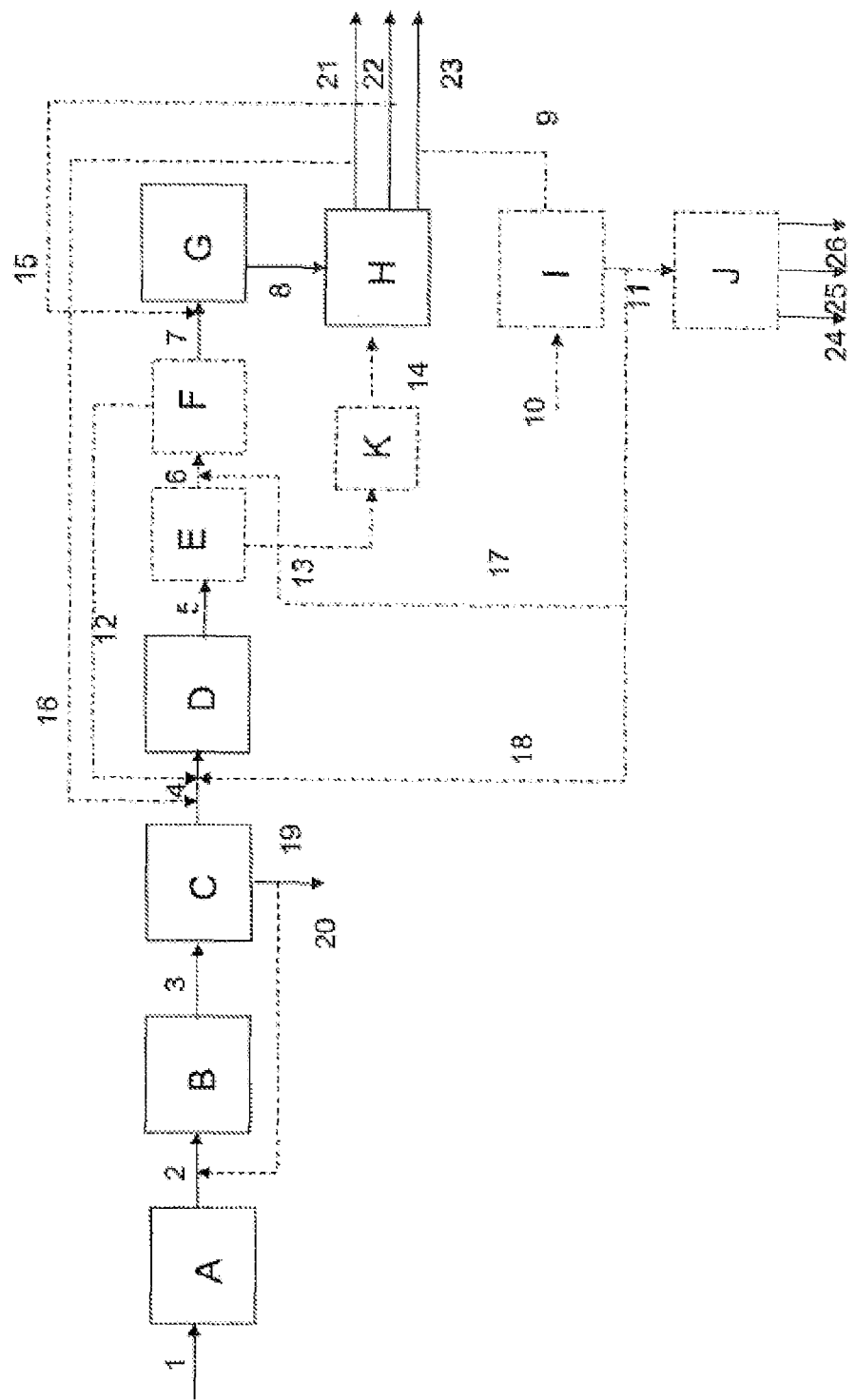
FIG. 1 diagrammatically shows the process for production of middle distillate bases from bioethanol of this invention in a second particular embodiment that includes a stage for treatment of the homogeneous catalytic system according to Method 3 described above and a separation stage between the first and second oligomerization stages d) and e).

The thus purified feedstock (pipe 2) is then sent into a reaction section (B) in which it undergoes a dehydration stage b) for producing an effluent that is for the most part ethylene and water. Said effluent that is for the most part ethylene is next sent into the section (C) via the pipe (3) in which it undergoes a separation stage c) in such a way as to separate at least a portion of the water that is formed during stage b) via the pipe (19) of the effluent that is for the most part ethylene, obtained from stage b).

According to a variant of the process for the invention shown in dotted lines, at least a portion of the aqueous effluent that is eliminated during the separation stage c) is recycled upstream from the reaction section (B), serving as a diluent of the purified bioethanol feedstock, via the pipe (20).

The effluent that is for the most part ethylene, obtained from the separation stage c) (pipe (4)) is sent into a reaction section (D) in which it undergoes a first oligomerization stage for producing at least one light olefinic effluent that comprises at least 80% by weight of olefins having four or more carbon atoms. According to one preferred embodiment that is shown in dotted lines, the effluent that is obtained from the oligomerization stage d) is then sent (pipe (5)) into a purification section (E), in which it undergoes a separation into a first effluent that comprises at least a portion of the C9+ olefinic compounds and also the homogeneous catalytic system (pipe 13) and into a second olefinic effluent that is free of the catalytic system (pipe (6)), whereby said separation is followed by the treatment of the effluent comprising at least a portion of the C9+ compounds and the homogeneous catalytic system by acid and/or basic washing or by use of the collection mass in section K.

Said C9+ olefinic effluent that is obtained from the purification stage next undergoes a drying stage that is not shown in the figure before being sent into the final fractionation zone (H) via the pipe (14). In the case where the treatment of the effluent that comprises at least a portion of the C9+ compounds and the homogeneous catalytic system is implemented by acid and/or basic washing, the aqueous effluent that comprises the homogeneous catalytic system is eliminated via the pipe (27).

Said olefinic effluent that is free of the homogeneous catalytic system and obtained from the purification section (E) via the pipe (6) next undergoes an optional separation stage in which said effluent is advantageously separated into at least one C4+ effluent (pipe (7)) and at least one light olefinic effluent (C2-C4) (pipe 12)), which is recycled in the first oligomerization stage d).

The effluent that is obtained from the optional separation zone (F) is sent via the pipe (7) into a reaction zone (G) in which it undergoes a second oligomerization stage e) that produces middle distillate hydrocarbon bases (pipe (8)).

The effluent that is obtained from oligomerization stage e) is next sent via the pipe (8) into a fractionation zone (H) in which it is separated into a light effluent that comprises the C2-C4 compounds via the pipe (21), into a gasoline fraction via the pipe (22), and into a middle distillate fraction (kerosene and/or gas oil via the pipe (23)).

In one preferred embodiment that is shown in dotted lines, at least a portion of said light effluent that comprises the C2 to C4 compounds obtained from the fractionation zone (H) is recycled in the first oligomerization stage d) via the pipe (16).

In one preferred embodiment that is shown in dotted lines, at least a portion of the gasoline fraction that is obtained from fractionation zone (H) is recycled in the second oligomerization stage e) via the pipe (15).

In one preferred embodiment shown in dotted lines, at least a portion of the middle distillate bases (pipe (9)) is sent into a section (I) for hydrogenation of the olefins that are produced, whereby said section is supplied by hydrogen via the pipe (10).

The effluent that is obtained from the optional hydrogenation stage via the pipe (11) for the most part contains hydrocarbons that can be upgraded and incorporated in the kerosene and gas oil pool. According to an embodiment that is shown in dotted lines, at least a portion of said effluent that is obtained from the optional hydrogenation stage is sent via the pipes (17) and (18) respectively into the oligomerization stages d) in such a way as to constitute a diluent of the feedstock and thus to stabilize the catalyst, and—in the effluent obtained from oligomerization stage d) at the level of the optional separation stage—in such a way as to improve the separation.

At least a portion of said effluent that is obtained from the optional hydrogenation stage is advantageously sent via the pipe (11) into a separation section (J) that makes possible fractionation into a kerosene fraction (pipe 24), into a gas-oil fraction (pipe 25), and into a fraction that has a boiling point that is greater than 360° C. (pipe 26).

In FIG. 2, the ethanol feedstock that is produced from a renewable source obtained from the biomass, called bioethanol, is introduced into a reaction zone (A) via the pipe (1) in which said feedstock undergoes a purification stage.

The thus purified feedstock (pipe 2) is then sent into a reaction section (B) in which it undergoes a stage b) for dehydration into an effluent that is for the most part ethylene and into an aqueous effluent. Said effluent that is for the most part ethylene obtained from stage b) is then sent into the section (C) via the pipe (3), in which it undergoes a separation stage c) in such a way as to separate at least a portion of the aqueous effluent that is formed during stage b) via the pipe (18) of the effluent that is for the most part ethylene, obtained from stage b).

According to a variant of the process of the invention shown in dotted lines, at least a portion of the aqueous effluent that is eliminated during separation stage c) is recycled upstream from the reaction section (B), serving as a diluent of the purified bioethanol feedstock, via the pipe (19).

The effluent that is for the most part ethylene obtained from the separation stage c) (pipe (4)) is sent into a reaction section (D) in which it undergoes a first oligomerization stage into at least one light olefinic effluent that comprises at least 80% by weight of olefins that have four or more carbon atoms. According to a preferred embodiment shown in dotted lines, the effluent that is obtained from the oligomerization stage d) is next sent (pipe (5)) into a purification section (E), in which it undergoes a purification stage by treatment of the homogeneous catalyst by acid or basic washing of the light olefinic effluent obtained from the first oligomerization stage d), whereby said homogeneous catalyst is separated and eliminated from said light olefinic effluent by separation of the aqueous phase in which it is solubilized via the pipe (26).

Said olefinic effluent that exits from the optional purification stage via the pipe (6) next undergoes an optional separation stage in the zone (F) in which said effluent is separated into at least one C4+ effluent (pipe (7)) and at least one light olefinic effluent (C2-C4) (pipe (12)), which is recycled in the first oligomerization stage d).

The C4+ olefinic effluent is separated from at least a portion and preferably all of the C9+ olefinic effluent in the optional separation zone (F) via the pipe (13). In this case, said C4+ olefinic effluent, separated from at least a portion and preferably all of said C9+ olefinic effluent, is advantageously sent via the pipe (7) into the second oligomerization zone (G), and at least a portion and preferably all of said C9+ olefinic effluent is advantageously sent directly into the final fractionation zone (H).

The effluent that is obtained from oligomerization stage e) is next sent via the pipe (8) into a fractionation zone (H) in which it is separated into a light effluent that comprises the C2-C4 compounds via the pipe (20), into a gasoline fraction via the pipe (21), and into a middle distillate fraction (kerosene and/or gas oil via the pipe (22).

In one preferred embodiment shown in dotted lines, at least a portion of said light effluent that comprises the C2 to C4 compounds obtained from the fractionation stage e) is recycled in the first oligomerization zone (D) via the pipe (15).

In one preferred embodiment shown in dotted lines, at least a portion of the gasoline fraction obtained from fractionation stage e) is recycled in the second oligomerization zone (G) via the pipe (14).

In one preferred embodiment shown in dotted lines, at least a portion of the middle distillate bases (pipe (9)) is sent into a section (I) for hydrogenation of the olefins that are produced, whereby said section is supplied by hydrogen via the pipe (10).

The effluent that is obtained from the optional hydrogenation stage via the pipe (11) for the most part contains hydrocarbons that can be upgraded and incorporated into the kerosene and gas oil pool. According to one embodiment that is shown in dotted lines, at least a portion of said effluent that is obtained from the optional hydrogenation stage is sent via the pipes (16) and (17) respectively into the oligomerization stages d) in such a way as to constitute a diluent of the feedstock and thus to stabilize the catalyst and into the effluent that is obtained from oligomerization stage d) at the optional separation stage in such a way as to improve the separation.

At least a portion of said effluent that is obtained from the optional hydrogenation stage is advantageously sent via the pipe (11) into a separation section (J) that makes possible the fractionation into a kerosene fraction (pipe 23), into a gas oil fraction (pipe 24), and into a fraction that has a boiling point that is greater than 360° C. (pipe 25).

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application No. 10/01954, filed May 6, 2010, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The following example illustrates the invention without limiting its scope.

EXAMPLE

Example 1 According to the Invention

Description of the Bioethanol Feedstock

The bioethanol feedstock that is used in the example is a bioethanol feedstock that has been treated by a series of stages of distillation and being run over molecular sieves so as to meet the following specifications and whose composition is given in Table 1:

TABLE 1

Composition of the Purified Bioethanol Feedstock

| Composition | Content in % by Weight |
|---|---|
| EtOH | 99% |
| Methanol | <0.05% |
| Butanol | <0.1% |
| Other Alcohols | <0.05% |
| Total Content of Alcohol Other than Ethanol, % by Weight | <0.2% |
| Oxidized Compounds Other than Alcohols | <0.1% |
| H2O | <1% |
| Total Cationic Impurities | <0.005% |
| Total Anionic Impurities | <0.005% |

Stage b): Dehydration of the Purified Feedstock

The purified feedstock next undergoes a stage for dehydration into ethylene and water in the presence of a zeolitic catalyst C1.

Preparation of the Catalyst C1

The dehydration catalyst of stage b) is prepared as described in the patent application US2009/088595.

It involves a ZSM-5-based zeolitic catalyst.

An emulsion is prepared by introducing the following into a 1-liter beaker: 244 g of water, 49 g of pore-forming agent that consists of isane, and 2.9 g of surfactant that consists of galoryl. The mixture is put on stir at 500 rpm for 15 minutes.

A suspension is prepared by introducing 2,198 g of permuted water and 69 g of nitric acid at 59.68% by weight into a 4-liter beaker, with the mixture being stirred at 400 rpm for 5 minutes. 450 g of PURAL SB3 (fire loss=26.10%) is added next, and the mixture {permuted water, nitric acid, and PURAL SB3} is stirred at 1,600 rpm for 14 minutes. 332 g of zeolite ZSM-5 in H form with an Si/Al ratio that is equal to 140, marketed by the Zeolyst Company, is then added to the mixture {permuted water, nitric acid, and PURAL SB3}, the resulting mixture is stirred at 1,600 rpm for 3 minutes, and then the emulsion formed by water, isane, and galoryl is added to said mixture. The combination is stirred under 1,600 rpm for 13 minutes, and then the stirring speed is reduced to 625 rpm for 70 minutes. The viscosity of said mixture is then measured by means of a plane-plane rheometer for a shear-speed gradient of $100\ s^{-1}$ and is equal to 270 mPa·s.

For shaping by drop coagulation, a 9.4-liter glass column is used. Said column is charged with 7 liters of an ammonia solution that has a concentration that is equal to 28 g/l, 0.4 liter of an ammonyl solution with 1% by mass, and 0.7 liter of isane. The column is topped by a draining pot that consists of nozzles, each being provided with a circular opening that has a diameter that is equal to 1 mm. The suspension is introduced into said draining pot, with the draining flow rate being such that 80 droplets are drained per minute and per nozzle. The droplets next fall into the isane phase and then into the ammonia phase at 28 g/l, with the isane phase-ammonia phase interface consisting of ammonyl. The thus obtained balls are placed in a ventilated box at ambient temperature for one night to carry out a first mild drying and then are placed in an oven for one night at 100° C. The dried balls are calcined for 2 hours in a muffle furnace at 600° C. The catalyst C1 whose textural and mechanical characteristics are provided in Table 2 is thus obtained. It has a mechanical strength such that the grain-to-grain crushing (EGG) is equal to 26 N.

TABLE 2

Textural and Mechanical Characteristics of the Catalyst C1.

| | C1 |
|---|---|
| BET Surface Area (m$^2$/g) | 321 |
| Hg Pore Volume (ml/g) | 0.41 |
| Hg Macropore Volume (ml/g) | 0.12 |
| Hg Mesopore Volume (ml/g) | 0.29 |
| Size of Spherical Balls (mm) | 1.8-2.2 |

Stage b) of the process according to the invention is implemented in such a way as to maximize the production of ethylene. Dehydration stage b) works in the presence of the zeolitic catalyst C1 described above and at a temperature of 400° C., at a pressure of 0.1 MPa, and at an hourly speed by weight of 5 h−1.

Dehydration stage b) produces a hydrocarbon effluent that is for the most part ethylene comprising water whose distribution is provided in Table 3.

TABLE 3

Distribution of the Effluent that is Produced During Stage b)

| Distribution | % by Weight Relative to the Ethanol Mass Introduced in Stage b) |
|---|---|
| Water | 39.5% by Weight |
| Hydrocarbon Effluent | 60% by Weight |
| Ethanol | 0.5% |

The composition of the effluent that is for the most part ethylene and that is produced during dehydration stage b) is measured by gas phase chromatography (GPC) and provided in Table 4.

TABLE 4

Composition of the Effluent that is for the Most Part Ethylene and that is Formed During the Dehydration of Ethanol

| Distribution | % by Weight Relative to the Total Mass of the Hydrocarbon Compounds and Hydroxycarbons that are Formed |
|---|---|
| Ethylene | 98.5% |
| Hydrocarbons that Have More than Three Carbon Atoms | 1.5% |
| Oxidized Compounds | <0.1% |

The conversion of the ethanol C$_2$H$_5$OH in stage b) is 99.5%. 591 kg/h of ethylene is obtained from 1,000 kg/h of purified bioethanol.

Stage c): Separation.

The effluent that is for the most part ethylene and is obtained from stage b) next undergoes a separation and purification series by being run over a column for washing with water, and then by being run over a column for washing with soda and in driers in such a way as to separate a portion of the water that is formed during stage b) of the ethylene effluent.

Stage d): Oligomerization.

The effluent that is obtained from separation stage c) is sent into the first oligomerization stage d) that operates in the presence of a homogeneous catalyst that comprises a bivalent nickel compound C2 described below and at a temperature of 45° C., at a pressure of 3 MPa.

Preparation of the Catalyst C2:

Preparation of the Nickel Solution:

0.43 g of nickel ethyl-2 hexanoate with 13% by weight of nickel is introduced into a 2.5-liter glass flask equipped with a bar magnet for stirring, and then the flask that is placed under argon atmosphere is carefully purged. 400 ml of pentane that is deoxidized and dried on a molecular sieve 3A, which is used as a solvent below, is introduced therein by means of a transfer needle. Stirring makes it possible to dissolve the nickel salt. Next, a solution that is prepared from 0.11 g of trifluoroacetic acid made up to 100 g with pentane is injected. The combination is placed, still while being stirred, in a thermostatic bath regulated at 30° C. Next, the solution that is obtained is diluted with pentane in such a way as to adjust the nickel concentration to 0.1630 g of Ni/Kg.

Preparation of the Solution of Co-Catalyst EtAlCl$_2$ (EADC):

The co-catalyst is dichloroethyl aluminum (EADC). It is used in solution in the n-hexane. A solution with 5 g of EADC/Kg is used.

The nickel solution is injected into the reaction unit using a pump (LEWA type). The dichloroethyl aluminum is injected separately using another pump.

Oligomerization Reaction:

The reactor is a cylinder that is 10 cm in diameter and 61 cm in height. The reactor is equipped with a recirculation loop. The temperature in the reactor is kept constant and controlled by water circulation in a double jacket around the recirculation loop. The level of liquid in the reactor is also controlled. The input of ethylene is done at the top of the reactor and with the flow rate being monitored. The solutions of catalysts (Ni and EADC), preserved under inert gas, are injected separately into the recirculation loop of the reactor with the flow rate being monitored. The Al/Ni molar ratio is set at 15. The percentage of EADC relative to the input feedstock is 0.020% by weight. The operating pressure in the reactor is on the order of 3 MPa, and the temperature is 45° C. The ethylene input is weighed.

At the output of the reactor, the analysis of the effluent is done on the gaseous phase by gas phase chromatography and on the liquid effluent that is weighed and analyzed by gas phase chromatography.

The composition of the light olefinic effluent that comprises at least 80% by weight of olefins having four or more carbon atoms obtained from stage b) is provided in Table 5.

TABLE 5

Composition of the Light Olefinic Effluent Obtained from the First Oligomerization Stage d)

| | % by Weight Relative to the Total Mass of the Olefins Contained in the Olefinic Effluent Produced at the End of Stage d) |
|---|---|
| C2 | 4 |
| C4+ | 96 |
| | Including 96% of C4-C8 |
| | 4% of C9+ |

The C4-C8 fraction consists of 54% by weight of C4 olefins, 36% by weight of C6 olefins, and 10% by weight of C8 olefins.

Treatment of the Catalytic System at the End of Oligomerization Stage d)

The effluent at the output of d) is neutralized by washing with a soda solution at 20% by weight in a stirred reactor. The organic phase that consists of liquid products of the reaction is separated by decanting and is analyzed. The homogeneous catalytic system is separated by elimination of the aqueous phase.

The impurities of the feedstock such as water and/or the other oxidized compounds are eliminated for the most part after being run over sieves 3A and 13X that are known to one skilled in the art.

At the end of the treatment stage of the catalytic system, 583 kg/h of olefins that have four or more carbon atoms are obtained from 1,000 kg/h of purified bioethanol introduced in stage b).

The effluent that is obtained from the stage for treatment of the catalytic system is sent to the second oligomerization stage e).

Stage e): Second Oligomerization Stage.

Oligomerization stage e) works in the presence of the catalyst C3 described below and at a temperature of 150° C., at an absolute pressure of 6.0 MPa, and at an hourly speed by weight of 0.7 h−1.

Preparation of the Catalyst C3 Used in the Second Oligomerization Stage e)

Preparation of the Catalyst C3

An aluminum hydroxide powder is mixed with a silica sol that is prepared by decationizing resin exchange, and then filtered on resin with porosity 2. The concentrations of silica sol and aluminum hydroxide powder are adjusted in such a way as to obtain a final composition of 80% $Al_2O_3$ and 20% $SiO_2$. The shaping is done in the presence of 15% nitric acid relative to the anhydrous product. The mixed paste is then extruded through a die with a diameter of 1.4 mm. The thus obtained extrudates are dried at 120° C., and then calcined at 550° C.

The composition of the effluent that is obtained from the second oligomerization stage is described in Table 6.

TABLE 6

Composition of the Olefinic Effluent that is Obtained from the Second Oligomerization Stage e)

| | % by Weight Relative to the Total Mass of the Exiting Effluent |
|---|---|
| C2 | 4 |
| C4+ | 96 |
| | Including 32% of C4-C8 |
| | 68% of C9+ |

The olefinic effluent C9+ has a T95 that is less than 360° C., with the T95 being the temperature at which 95% of the products are evaporated.

The effluent that is obtained from the second oligomerization stage e) next undergoes a fractionation stage f) in such a way as to separate it into a light effluent that comprises the C2-C4 compounds, a gasoline fraction, and a middle distillate fraction (gas oil and kerosene).

The yields of the different fractions are indicated in Table 7.

TABLE 7

Yields

| | % by Weight |
|---|---|
| C2-C4 | 12 |
| Gasoline (50-150° C.) | 23 |
| Kerosene (150-280° C.) | 51 |
| Gas Oil (280-360° C.) | 14 |

At the end of this stage, 309 kg/h of kerosene and 84.5 kg/h of diesel are obtained from 1,000 kg/h of purified bioethanol that is introduced in stage b).

The invention claimed is:

1. A process for the production of a kerosene hydrocarbon base from an ethanol feedstock that is produced from a renewable source that is obtained from biomass, said process comprising:
    a) a stage for purification of said ethanol feedstock,
    b) a stage for dehydration of the purified ethanol feedstock obtained from purification stage a) into an effluent, wherein said effluent is for the most part ethylene and also comprises water, and wherein said dehydration is conducted in the presence of an amorphous acid catalyst or a zeolitic acid catalyst,
    c) at least one stage for separation of the water that is present in said effluent obtained from dehydration stage b),
    d) a first stage for oligomerization of at least a portion of the effluent obtained from separation stage c) to form at least one olefinic effluent that comprises at least 80% by weight of olefins that have four or more carbon atoms, relative to the total mass of the olefins that are contained in said least one olefinic effluent, and wherein oligomerization is performed in the presence of a homogeneous catalyst that comprises at least one bivalent nickel compound, said homogeneous catalyst being soluble in a liquid phase of ethylene and its oligomerization products,
    e) a second stage for oligomerization of at least a portion of the olefinic effluent obtained from first oligomerization stage d), to produce an effluent comprising middle distillate hydrocarbon bases, wherein oligomerization in the second oligomerization stage e) is performed in the presence of an amorphous catalyst, and wherein said second oligomerization stage e) is performed in at least one fixed-bed reactor operating at a temperature of between 50 and 400° C., at an absolute pressure of between 2 and 15 MPa, and at an hourly speed by weight of between 0.1 and 50 h−1, and
    f) a stage for fractionation of the effluent obtained from the second oligomerization stage e) to obtain said kerosene hydrocarbon base.

2. The process according to claim 1, wherein the homogeneous catalyst used in first oligomerization stage d) which comprises at least one bivalent nickel compound, further comprises at least one hydrocarbyl-aluminum halide, and at least one Brönsted organic acid.

3. The process according to claim 2, wherein said at least one bivalent nickel compound is nickel octoate, nickel ethyl-2-hexanoate, nickel decanoate, nickel stearate, nickel oleate, nickel salicylate, or nickel hydroxydecanoate, taken by themselves or in a mixture.

4. The process according to claim 2, wherein said at least one hydrocarbyl-aluminum halide is selected from among the hydrocarbyl-aluminum dihalide of the formula AlRX2, in which R is a hydrocarbyl radical and X is fluorine, chlorine, bromine or iodine, taken by themselves or in a mixture.

5. The process according to claim 2, wherein said at least one Brönsted organic acid is a halogenocarboxylic acid of the formula RCOOH in which R is a halogenated alkyl radical that contains at least one alpha-halogen atom of the group —COOH and has a total of two to ten carbon atoms.

6. The process according to claim 1, in which all of said at least one olefinic effluent produced during the first oligomerization stage d) is sent directly into the second oligomerization stage e).

7. The process according to claim 1, in which said at least one olefinic effluent that is produced during the first oligomerization stage d) undergoes at least one stage for treatment of said homogeneous catalyst and/or at least one stage for separation before being sent into the second oligomerization stage e).

8. The process according to claim 7, in which said stage for treatment of said homogeneous catalyst is implemented by the use of collection mass or by treatment of the at least one olefinic effluent obtained from the first oligomerization stage d), neutralized or not, and that contains said homogeneous catalyst by an acid and/or a base.

9. The process according to claim 7, in which said stage for treatment of said homogeneous catalyst is implemented by the separation of said at least one olefinic effluent obtained from the first oligomerization stage d), neutralized or not by a base, into a first effluent that comprises at least a portion of the olefinic compounds C9+ and also said homogeneous catalyst, and a second olefinic effluent that is free of said homogeneous catalyst, whereby said separation is followed by the treatment of the first effluent comprising at least a portion of the olefinic compounds C9+ and said homogeneous catalyst by acid and/or basic washing or by use of collection mass.

10. The process according to claim 7, in which said separation stage is implemented between said stage for treatment of said homogeneous catalyst and the second oligomerization stage e), in such a way as to separate said at least one olefinic effluent obtained from the first oligomerization stage d) into at least one olefinic effluent that has four or more carbon atoms and at least one light olefinic effluent (C2-C4).

11. The process according to claim 10, in which all of said C2-C4 light olefinic effluent is recycled to the first oligomerization stage d).

12. The process according to claim 1, in which the second oligomerization stage e) is operated at a temperature of between 100 and 300° C., at a pressure of between 2 and 6 MPa, and at an hourly speed by weight of between 0.1 and 5 $h^{-1}$.

13. The process according to claim 1, in which at least a portion of the kerosene hydrocarbon base obtained from fractionation stage f) undergoes a stage for hydrogenation of olefins that are produced from the oligomerization stages, wherein said hydrogenation is performed in the presence of a catalyst that comprises palladium or nickel, taken by themselves or in a mixture, and an alumina, silica, or silica-alumina substrate.

14. The process according to claim 13, further comprising a separation stage following the hydrogenation stage to produce a kerosene fraction and/or a gas oil fraction and/or a fraction that has a boiling point that is higher than 360° C.

15. The process according to claim 1, wherein the amorphous catalyst used in the second oligomerization stage e) comprises an amorphous mineral material selected from silica-aluminas and siliceous aluminas.

16. The process according to claim 1, wherein the amorphous catalyst used in the second oligomerization stage e) is in the form of extrudates having a size of between 1 and 10 mm.

17. The process according to claim 1, wherein dehydration stage b) is operated at a temperature of between 250 and 600° C, at an absolute pressure of between 0.1 and 5 MPa, and at an hourly speed by weight of between 0.1 and 50 $h^{-1}$.

18. The process according to claim 17, wherein the dehydration stage b) is operated at a temperature of between 300 and 500° C, at an absolute pressure of between 0.1 and 1 MPa, and at an hourly speed by weight of between 0.5 and 15 $h^{-1}$.

19. The process according to claim 1, wherein said effluent of dehydration stage b) comprises at least 97% by weight of ethylene relative to the total mass of the carbon compounds that are formed and present in said effluent.

20. The process according to claim 1, wherein conversion of the purified ethanol feedstock in stage b) is greater than 90%.

21. The process according to claim 2, wherein said at least one hydrocarbyl-aluminum halide is selected from dichloroethylaluminum, dichloroisobutylaluminum and dibromoethylaluminum, and said at least one Brönsted organic acid is selected from trifluoroacetic, difluoroacetic, fluoroacetic, trichloroacetic, dichloroacetic, and chloroacetic acids.

22. The process according to claim 2, wherein the homogeneous catalyst used in first oligomerization stage d) further comprises at least one carboxylic acid anhydride of formula $(RCO)_2O$ in which R is a hydrocarbyl radical that can optionally contain one or more halogen atoms.

23. The process according to claim 2, wherein in the homogeneous catalyst used in first oligomerization stage d) the molar ratio of the hydrocarbyl-aluminum halide to the nickel compound, expressed by the Al/Ni ratio, is 2/1 to 50/1, and the molar ratio of the Brönsted acid to the nickel compound is 0.25/1 to 10/1.

24. The process according to claim 22, wherein in the homogeneous catalyst used in first oligomerization stage d) the molar ratio of the hydrocarbyl-aluminum halide to the nickel compound, expressed by the Al/Ni ratio, is 2/1 to 50/1, the molar ratio of the Brönsted acid to the nickel compound is 0.25/1 to 10/1, and the molar ratio of the carboxylic acid anhydride to the nickel compound is between 0.001/1 and 1/1.

25. The process according to claim 1, wherein the water content of the effluent obtained from separation stage c) that is sent to said first oligomerization stage d) is between 0 and 500 ppm.

26. The process according to claim 1, wherein the olefinic effluent obtained from said first oligomerization stage d) comprises at least 90% by weight of olefins that have four or more carbon atoms, relative to the total mass of the olefins that are contained in said olefinic effluent obtained from said first oligomerization stage d).

27. The process according to claim 1, wherein the olefinic effluent obtained from said first oligomerization stage d) comprises less than 10% by weight of unreacted ethylene, relative to the total mass of the olefins that are contained in said olefinic effluent obtained from said first oligomerization stage d).

28. The process according to claim 1, wherein the olefinic effluent obtained from said first oligomerization stage d) comprises less than 10% by weight of olefins that have nine or more carbon atoms, relative to the total mass of the olefins that are contained in said olefinic effluent obtained from said first oligomerization stage d).

29. The process according to claim 1, wherein the effluent obtained from the first oligomerization stage d), prior to being sent to the second oligomerization stage e), is sent to a purification section, in which it undergoes separation into: (a) a first effluent that comprises at least a portion of the C9+ olefinic compounds and the homogeneous catalyst, and (b) a second olefinic effluent that is free of the homogeneous catalyst, and said first effluent comprising at least a portion of the C9+ compounds and the homogeneous catalytic system is treated by acid and/or basic washing or by use of a collection mass, and said second olefinic effluent that is free of the homogeneous catalyst undergoes a separation stage in which said second olefinic effluent is separated into at least one C4+ effluent and at least one light olefinic effluent, and said at least one light olefinic effluent is recycled to the first oligomerization stage d), and said at least one C4+ effluent is to the second oligomerization stage e).

30. The process according to claim 1, wherein in the fractionation stage f the effluent obtained from the second oligomerization stage e) is fractionated into (a) a light effluent that comprises the C2-C4 compounds, (b) a gasoline fraction, and (c) said kerosene hydrocarbon base, and at least a portion of said light effluent that comprises the C2 to C4 compounds obtained from the fractionation stage f) is recycled to the first oligomerization stage d).

31. The process according to claim 30, wherein at least a portion of said gasoline fraction obtained from fractionation stage f) is recycled to the second oligomerization stage e).

32. The process according to claim 1, wherein the olefinic effluent obtained from said first oligomerization stage d) is sent to a purification stage (E), in which the olefinic effluent obtained from said first oligomerization stage d) undergoes a purification by treatment of the homogeneous catalyst by acid or basic washing and said homogeneous catalyst is separated and eliminated from said olefinic effluent by separation of the aqueous phase in which it is solubilized, said olefinic effluent is discharged said purification stage (E) and sent to separation stage (F) in which said olefinic effluent is separated into at least one C4+ olefinic effluent, at least one light olefinic effluent (C2-C4), and a C9+ olefinic effluent, and said at least one light olefinic effluent (C2-C4) is recycled to said first oligomerization stage d), said C9+ olefinic effluent is sent directly to the fractionation stage f), and said C4+ olefinic effluent is sent to said second oligomerization stage e), wherein in the fractionation stage f) the effluent obtained from the second oligomerization stage e) is fractionated into (a) a light effluent that comprises the C2-C4 compounds, (b) a gasoline fraction, and (c) said kerosene hydrocarbon base, at least a portion of said light effluent that comprises the C2 to C4 compounds obtained from the fractionation stage f) is recycled to the first oligomerization stage d), and at least a portion of said gasoline fraction obtained from fractionation stage f) is recycled to the second oligomerization stage e).

* * * * *